US00PP28319P3

(12) United States Plant Patent
Smith

(10) Patent No.: US PP28,319 P3
(45) Date of Patent: Aug. 22, 2017

(54) ***CHRYSANTHEMUM* PLANT NAMED 'CIFZ0032'**

(50) Latin Name: *Chrysanthemum×morifolium*
Varietal Denomination: CIFZ0032

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,446

(22) Filed: May 6, 2016

(65) Prior Publication Data

US 2016/0338239 P1 Nov. 17, 2016

Related U.S. Application Data

(60) Provisional application No. 62/161,924, filed on May 15, 2015.

(51) Int. Cl.
*A01H 5/02* (2006.01)

(52) U.S. Cl.
USPC ..... Plt./290

(58) Field of Classification Search
USPC ..... Plt./290
CPC ..... A01H 5/0255
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0032' particularly distinguished by the medium-sized bronze, decorative-type flowers, medium sized plant with a very round plant habit, and with the natural flowering season in mid September.

1 Drawing Sheet

Latin name of the genus and species of the plant claimed: *Chrysanthemum×morifolium.*

Varietal denomination: 'CIFZ0032'.

BACKGROUND OF THE NEW PLANT

The present invention comprises a new *Chrysanthemum*, botanically known as *Chrysanthemum×morifolium*, and hereinafter referred to by the variety name 'CIFZ0032'.

'CIFZ0032' is a product of a planned breeding program. The new cultivar has medium-sized bronze, decorative-type inflorescences, medium sized plant with a very round plant habit, and with the natural flowering season in mid September.

'CIFZ0032' originated from a hybridization made in December 2010 in a controlled area in Amatitlan, Guatemala. The female parent was the commercial plant 'Zanmusunet', also known as 'Sunset Orange', U.S. Plant Pat. No. 20,475, with a more orange hue of the young flower, a natural flowering response about one week slower, a less rounded plant habit and taller plant size when compared to 'CIFZ0032'.

The male parent of 'CIFZ0032' was the unpatented, proprietary plant designated as 'G0519L1', with purple, decorative-type inflorescences, that are somewhat smaller in size, a similar plant habit, but with smaller overall plant size when compared to 'CIFZ0032'.

The resultant seed was sown in July 2011 in Gilroy, Calif., USA. 'CIFZ0032' was selected as a single flowering plant within the progeny of the stated cross on Nov. 1, 2011 in Monroeville, N.J., USA.

The first act of asexual reproduction of 'CIFZ0032' was accomplished when vegetative cuttings were propagated from the initial selection in January 2012 in a greenhouse in Monroeville, N.J.

BRIEF SUMMARY OF INVENTION

Horticultural examination of plants grown from cuttings of the plant initiated in the spring of 2012 in Monroeville, N.J., and continuing thereafter, has demonstrated that the combination of characteristics as herein disclosed for 'CIFZ0032' are firmly fixed and are retained through successive generations of asexual reproduction.

'CIFZ0032' has not been observed under all possible environmental conditions. The phenotype may vary significantly with variations in environment such as temperature, light intensity and day length.

A Plant Breeder's Right for this cultivar was applied for in Canada on Apr. 27, 2015, No. 15-8621.

'CIFZ0032' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

Figure 1:
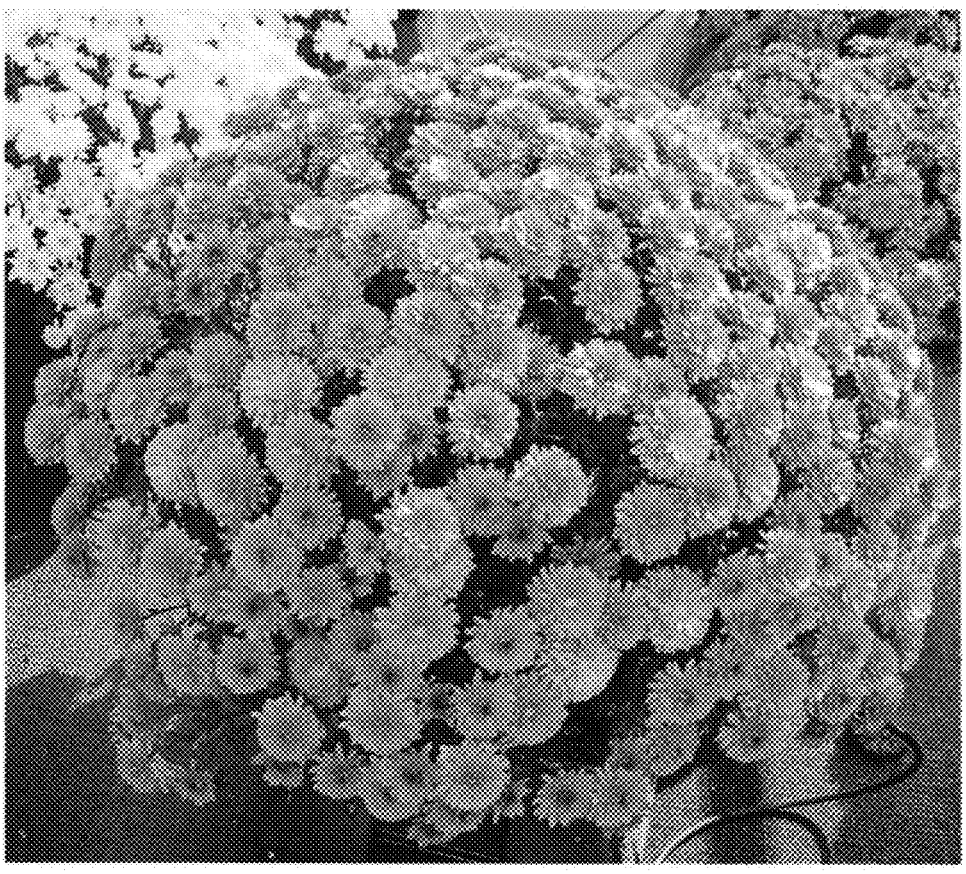
Figure 2:
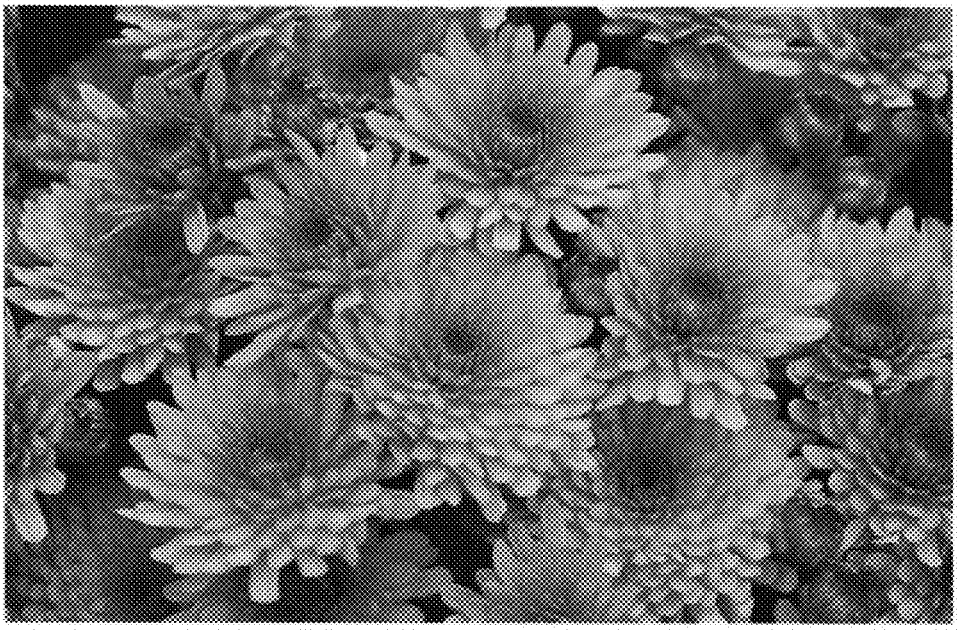

The accompanying photographic drawings show typical flower and foliage characteristics of 'CIFZ0032' with colors being as true as possible with an illustration of this type. The photographic drawings, taken Sep. 4, 2015, show in FIG. 1 a flowering potted plant of the new variety from an outdoor trial in Enkhuizen, The Netherlands, and in FIG. 2 an up close of an inflorescence of the same.

These plants were about 14 weeks of age. One rooted cutting in a 19 cm pot had been planted in week 21st, no pinch. Plants started flowering by about half august.

DETAILED BOTANICAL DESCRIPTION

The measurements were taken in Enkhuizen, The Netherlands, in August 2015 on plants that were growing in 19 cm pot size, trials with short days treatment: shade from week 29 until week 34. Culture of these plants started week 21 2015, cutting date, no pinching, in Enkhuizen, The Netherlands. The potting date is week 23 2015.

Color references are made to The Royal Horticultural Society Colour Chart (R.H.S.) 2001.

TABLE 1

DIFFERENCES BETWEEN THE NEW VARIETY 'CIFZ0032' AND TWO MOST SIMILAR VARIETIES:

| | 'CIFZ0032' | 'EMPIRE HARMONY', commercially 'Harmony Bronze Bicolor', U.S. Plant Pat. No. 11,830 |
|---|---|---|
| Flower color: | Somewhat darker hue | Somewhat lighter hue |
| Flower size: | Larger | Smaller |
| | 'CIFZ0032' | 'ZANMUBEDAZ', (U.S. Plant Pat. No. 23,014), also known as 'Bedazzled Bronze' |
| Flower color: | Deeper bronze hue | Lighter bronze hue |
| Plant habit: | Similar habit, but larger in size | Smaller plant size |

The plant descriptions and measurements were taken outdoors in Enkhuizen, The Netherlands in August 2015 on about 14 weeks old plants. Rooted cuttings had been planted, 1 plant per pot, in 19 cm pots in week 23 2015. The plants were not pinched. Shade, or short days, started week 29 until week 34.

Plant:

*Form, growth and habit.*—Herbaceous garden-type, stems upright and outwardly spreading, freely branching, strong and moderately vigorous growth habit.

*Plant height (above soil).*—14 cm.

*Plant height (inflorescence included).*—27-30 cm.

*Plant width.*—43-45 cm.

Roots:

*Number of days to initiate roots.*—About 4 days at about 22 degrees C.

*Number of days to produce a rooted cutting.*—14-16 days at 27 degrees C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 137A.

*Mature leaf, color lower surface.*—RHS 137C.

*Length.*—3.5-4 cm.

*Width.*—2-3 cm.

*Shape.*—Ovate, with distinct lobes.

*Base shape.*—Attenuate and asymmetric.

*Apex shape.*—Acute.

*Margin.*—3 to 5 lobed (palmate), edge serrate.

*Texture, upper surface.*—Hirsute.

*Texture, lower surface.*—Hirsute.

*Color of veins, upper surface.*—RHS 147B.

*Color of veins, lower surface.*—RHS 147B.

*Pattern of veining.*—Palmate.

*Petiole color.*—RHS 147C.

*Petiole Length.*—1.1-1.6 cm.

*Diameter.*—0.15-0.3 cm.

*Texture.*—Densely covered with hairs, tomentose.

Stem:

*Quantity of main branches per plant.*—8-12.

*Color of stem.*—RHS 147B.

*Length of stem.*—16-18 cm.

*Diameter.*—0.5 cm.

*Length of internodes.*—3 cm.

*Texture.*—Densely covered with hairs.

*Color of peduncle.*—RHS 147B.

*Length of peduncle.*—3-6 cm.

*Peduncle diameter.*—0.2 cm.

*Texture.*—Densely covered with hairs.

Inflorescence:

*Type.*—Compositae, solitary, decorative-type inflorescences borne terminally above foliage, spoon tipped ray florets arranged acropetally on a capitulum giving a daisy-eyed double flower form.

*Quantity of short days to flowering (response time).*—Approximately six weeks.

*Natural season flowering.*—Mid September.

*Quantity of inflorescences per plant.*—300-400 (roughly).

*Lastingness of individual blooms on the plant.*—About five weeks from first color.

*Fragrance.*—Slightly spicy.

Bud (when showing color):

*Color.*—187B.

*Length.*—1 cm.

*Width.*—1 cm.

*Shape.*—Oblate (almost globular).

Immature inflorescence:

*Diameter.*—3 cm.

*Color of ray florets, upper surface.*—RHS 172A to 172B.

*Color of ray florets, lower surface.*—Close to RHS 173A.

Mature inflorescence:

*Diameter.*—3.5-4 cm.

*Depth.*—1 cm.

*Total diameter of disc.*—0.3-1 cm.

*Receptacle color.*—RHS 147B (deep green).

*Receptacle height.*—0.4-0.5 cm.

*Receptacle diameter.*—1.6 cm.

Ray florets:

*Average quantity of florets.*—Between 400-500 in several whorls.

*Color of florets, upper surface (adaxial).*—Slightly more brownish than RHS N172A.

*Color lower surface (abaxial).*—RHS 173A.

*Length.*—1.9 cm.

*Width/diameter.*—0.5 cm; 0.1 cm for the tube at the base.

*Shape.*—All spatulate when mature.

*Apex shape.*—Mostly obtuse.

*Base shape.*—Tube.

*Margin.*—Entire, small incisions may occur at the tip.

*Texture, upper surface.*—Papillate.

*Lower surface.*—Papillate.

Disc florets:

*Average quantity of florets.*—Between 200-400.

*Color of florets, upper surface.*—150D.

*Length.*—0.5 cm.

*Width.*—0.2 cm.

*Apex shape*.—Slightly dentate.
*Base shape*.—Tube.
*Margin*.—Entire, small incisions may occur at the tip.
*Texture, upper surface*.—Papillose.

Phyllaries:
*Quantity*.—20-10.
*Color, upper surface*.—RHS 147B.
*Color, lower surface*.—RHS 147B.
*Length*.—0.7 cm.
*Width*.—0.2-0.3 cm.
*Shape*.—Lanceolate.
*Apex shape*.—Acute.
*Base*.—Fused.
*Margins*.—Entire.
*Texture, upper surface*.—glabrous.
*Texture, lower surface*.—densely covered.

Reproductive organs:
*Pistil*.—One.
*Length*.—0.3-0.5 cm.
*Style color*.—RHS 7D.
*Style length*.—0.2-0.3 cm.
*Stigma color*.—RHS 7C.
*Stigma shape*.—Bi-parted.
*Ovary color*.—RHS 1D.
*Ovary length*.—0.15 cm.
*Ovary width*.—0.1 cm.

Androecium:
*Stamens*.—1, found on only disc florets.
*Color of filaments*.—RHS 2B.
*Length filaments*.—0.15-0.2 cm.
*Anther color*.—RHS 13A.
*Anther length*.—0.15-0.2 cm.
*Anther shape*.—Oval to club shaped.
*Color of pollen*.—RHS 13A.
*Pollen amount*.—Moderate.
*Fertility/seed set*.—Has not been observed to date.
*Disease/pest resistance*.—Has not been observed to date.

What is claimed is:

1. A new and distinct variety of *Chrysanthemum* plant named 'CIFZ0032' substantially as illustrated and described herein.

* * * * *